United States Patent [19]
Hughes

[11] Patent Number: 5,567,428
[45] Date of Patent: Oct. 22, 1996

[54] TOPICAL PERSONAL CARE COMPOSITION CONTAINING POLYSILOXANE-GRAFTED ADHESIVE POLYMER AND DRYING AID

[75] Inventor: Kendrick J. Hughes, Cincinnati, Ohio

[73] Assignee: The Procter & Gamble Company, Cincinnati, Ohio

[21] Appl. No.: 566,599

[22] Filed: Dec. 4, 1995

Related U.S. Application Data

[63] Continuation of Ser. No. 405,415, Mar. 15, 1995, abandoned, which is a continuation of Ser. No. 113,570, Aug. 27, 1993, abandoned.

[51] Int. Cl.$^6$ .............................. A61K 6/00; A61K 7/00; A61K 31/74
[52] U.S. Cl. ................. 424/401; 424/61; 424/70.12; 424/47; 424/443; 424/445; 424/447; 424/449; 424/78.02; 424/DIG. 1; 424/ DIG. 2
[58] Field of Search ............................... 424/401, 61, 70, 424/71, 47, 443, 445, 447, 449, 78.02, DIG. 1, DIG. 2

[56] References Cited

U.S. PATENT DOCUMENTS 4,925,659  5/1990  Grollier et al. ............................ 424/78

FOREIGN PATENT DOCUMENTS 0408311  1/1991  European Pat. Off. .

OTHER PUBLICATIONS

Todd et al "Volatile silicone fluids for cosmetic formulations" Cosmetics and Toiletries vol. 91, Jan, 1976, pp. 29–32.

*Primary Examiner*—Nathan M. Nutter
*Attorney, Agent, or Firm*—Leonard W. Lewis; Anthony D. Sabatelli; David K. Dabbiere

[57] ABSTRACT

Provided is a topical personal care composition, having improved drying time, said composition comprising: (a) a polysiloxane-grafted adhesive polymer; (b) a volatile, water insoluble solvent for said polysiloxane-grafted polymer; (c) a nonvolatile drying aid for said polysiloxane-grafted polymer which is soluble in said volatile solvent (b) at 45° C. and is water insoluble at 25° C., and is selected from the group consisting of silicone fluids and waxes having from 1 to about 100 siloxy units, silanes, and silicone resins and mixtures thereof; wherein the weight ratio of said polysiloxane-grafted polymer (a) to said drying aid (c) is about 100:1 or less.

23 Claims, No Drawings

TOPICAL PERSONAL CARE COMPOSITION CONTAINING POLYSILOXANE-GRAFTED ADHESIVE POLYMER AND DRYING AID

This is a continuation of application Ser. No. 08/405,415, filed Mar. 15, 1995, and now abandoned which is a continuation of application Ser. No. 08/113,570, filed Aug. 27, 1993, and now abandoned.

TECHNICAL FIELD

The present invention relates to topical personal care compositions containing a polysiloxane-grafted adhesive polymer and a water insoluble volatile solvent.

BACKGROUND OF THE INVENTION

The use of adhesive polymers in topical personal care products is of increasing importance. In the hair care area, adhesive polymers can provide hair hold and style hold benefits. In other areas, adhesive polymers can be used for skin conditioning and for delivery of active materials to the skin and/or hair, e.g., cosmetic actives and medicinal actives. In general, adhesive polymers form films upon drying that can provide the hair with improved style hold, and can be used to provide the skin with modified feel, appearance, or protection, or provide delivery of cosmetic or medicinal actives. Although conventional adhesive polymers can be used, such polymers tend to make the hair or skin feel either stiff or tacky, or both. More recently, polysiloxane-grafied adhesive polymers have been discussed for treatment of hair and skin. Polysiloxane-grafted adhesive polymers can provide the same benefits as conventional adhesive polymers. However, they can do so while also imparting a softer, less stiff feel than such conventional adhesive polymers subsequent to application and drying.

Polysiloxane-grafted polymers are disclosed for use in EPO Application 90307528.1 published Jan. 16, 1991 as EPO Publication 0 408 311 A2, Hayama, et al., U.S. Pat. No. 5,061,481, issued Oct. 29, 1991, Suzuki et al., U.S. Pat. No. 5,106,609, Bolich et al., issued Apr. 21, 1992, U.S. Pat. No. 5,100,658, Bolich et al., issued Mar. 31, 1992, U.S. Pat. No. 5,100,657, Ansher-Jackson, et al., issued Mar. 31, 1992, U.S. Pat. No. 5,104,646, Bolich et al., issued Apr. 14, 1992, and Adhesive compositions containing film-forming polysiloxane-grafted polymers are also disclosed in U.S. Pat. No. 4,728,571, issued Mar. 1, 1988, Clemens et al., U.S. Pat. No. 5,021,477, issued Jun. 4, 1991, Garbe et al., U.S. Pat. No. 4,981,902, issued Jan. 1, 1991, Garbe et al., U.S. Pat. No. 4,988,506, issued Jan. 29, 1991, Mitra et al., and U.S. Pat. No. 4,981,903, Mitra et al., issued Jan. 1, 1991, Mitra et al.

Polysiloxane-grafted adhesive polymers are useful in a wide variety of hair care and skin care products, including hair hold products and hair setting products, hair conditioning products such as hair rinses, and leave-on conditioners, and shampoos. Polysiloxane-grafted polymers are also useful in skin care products such as cosmetics, skin conditioners, sunscreen products, skin tint products, and topical medicaments for delivery of medicinal active materials to the skin.

A preferred method for formulating polysiloxane-grafted adhesive polymers into compositions is in a volatile solvent. It is especially desirable to utilize hydrophobic solvents, such as silicone fluids. Such compositions can be formulated as single phase or multiple phase products. For multiple phase compositions, the dispersed phase of the polysiloxane-grafted adhesive polymer and volatile solvent is typically dispersed throughout a carrier phase in the form of droplets. Typically the carrier phase comprises water, monohydric alcohols, or a mixture thereof.

Whereas a great many benefits can be obtained through the use of polysiloxane-grafted adhesive polymers in compositions such as the ones described above, it remains desirable to further improve such compositions. In particular, it would be desirable to decrease the amount of time which is required for these compositions to dry once they have been applied. This would reduce the period during which stickiness or tackiness could be felt by users subsequent to application of the composition. It would also allow stronger cohesive performance, e.g., hair hold, to be achieved in a shorter period of time since adhesive performance increases as the polymer phase dries.

It would be especially desirable to provide decreased drying time for hair styling compositions without any substantial loss of hair hold performance once the composition is dried to completion. It would further be desirable to even increase the hair hold performance of films formed by the polysiloxane-grafted polymer.

The objects of this invention are to provide compositions and methods for fulfilling these goals. These objects and other benefits as may be apparent to those skilled in the art can be achieved through the present invention, which is described in the following Summary of the Invention and Detailed Description of the Invention and which is defined in the claims which follow.

Unless otherwise indicated, all percentages and ratios are by weight. All weight percentages are calculated based upon the total weight of the composition unless it is otherwise indicated. The invention hereof can comprise, consist of, or consist essentially of the essential elements and limitations of the invention described herein as well as any of the additional ingredients, components, or limitations described herein.

All documents referred to herein, including all patents, patent applications, and printed publications, are hereby incorporated by reference in their entirety into this disclosure.

SUMMARY OF THE INVENTION

The present invention provides a topical personal care composition, said composition comprising:

(a) a polysiloxane-grafted adhesive polymer;

(b) a volatile, water insoluble solvent for said polysiloxane-grafted polymer;

(c) a nonvolatile drying aid for said polysiloxane-grafted polymer which is soluble in said volatile solvent (b) at 45° C. and is water insoluble at 25° C., and is selected from the group consisting of silicone fluids and waxes having from 1 to about 100 siloxy units, silanes, and silicone resins and mixtures thereof;

wherein the weight ratio of said polysiloxane-grafted polymer (a) to said drying aid (c) is about 100:1 or less.

In preferred embodiments, the compositions hereof further comprise a carrier in which the mixture of polysiloxane grafted polymer, volatile solvent for the polymer, and drying aid from a separate phase which is dispersed. The carrier is preferably an aqueous or hydroalcoholic carrier.

The present invention further provides a method for making compositions containing polysiloxane-grafted adhesive polymers dispersed in aqueous—and/or monohydric alcohol-based carriers with decreased polymer drying time. This method comprises the steps of:

(a) preparing a premix of (i) a polysiloxane-grafted adhesive polymer; (ii) a volatile, water insoluble solvent for said polymer; and (iii) a drying aid for said polymer, selected from the group consisting of silicone fluids and waxes having from 1 to about 100 siloxy units, silicone resins, and silanes, and mixtures thereof, which is soluble in said solvent at 45° C. and is water insoluble at 25° C., wherein the weight ratio of said polysiloxane grafted polymer to said drying aid is about 100:1 or less; and (b) forming a dispersion of the premix solution of (a) into an aqueous or hydroalcoholic carrier.

The present invention further relates to a method of styling hair or forming an adhesive film on the skin, or nail, comprising the steps of: (a) applying an effective amount of a composition of the present invention for achieving the intended purpose to the hair, skin, or nail such as providing style hold to the hair or forming a film over the skin or nail (e.g. fingernail or toenail) and (b) drying said composition. In a particularly preferred embodiment, the composition is dried with the aid of a heat source providing a surface temperature of about 45° C. or higher.

By way of explanation without intending to be necessarily limited by theory, it is believed that the presence of the silicone-containing drying aid in these compositions speeds drying of the volatile solvent and, consequently, speeds drying and curing of the adhesive polymer to a less sticky, tacky condition. It is believed that upon deposition to the intended surface (e.g., hair, skin, or nails), the drying aid migrates or orients itself at the air interface. The presence of the drying aid facilitates continued evaporation of volatile solvent that would otherwise be trapped beneath the surface of the film, thus providing an overall decrease in drying time. Final polymer film strength can therefore be achieved earlier than without benefit of the present invention. Compositions of the present invention containing polysiloxane-grafted adhesive polymers dried with the aid of silicone resin or other drying aids which form solids upon drying may also provide increased hair hold performance.

The benefits of decreased drying time in the present invention are particularly noticeable when the surface to which the compositions hereof are applied, e.g., the hair or skin, are dried at elevated temperature such as with a forced air electric dryer or curling iron. Temperatures at the spot such a device is directed or applied typically reach about 45° C. or higher, and can easily reach 60°–70° C., or higher. The rate at which compositions hereof utilize the drying aid relative to similar compositions without the drying aid, is particularly enhanced at such elevated temperatures.

In addition to personal care products, such as but not limited to hair styling products, skin care products, and cosmetics, the present invention can be utilized in a wide variety of other adhesive products. These can include, but are not limited to, glue and other bonding materials, tape, release coatings, paint etc.

DETAILED DESCRIPTION OF THE INVENTION

The essential components and limitations of the present invention, as well as the preferred and a variety of optional components, limitations, and embodiments, are described below.

Polysiloxane-Grafted Adhesive Polymer

The compositions of the present invention essentially comprise a polysiloxane-grafted adhesive polymer. The compositions hereof will generally comprise from about 0.1% to about 10%, preferably from 0.5% to about 8%, more preferably from about 1.0% to about 8%, by weight of the composition, of the polysiloxane-grafted adhesive polymer. It is not intended to exclude the use of higher or lower levels of the polymers, as long as an effective amount is used to provide adhesive or film-forming properties to the composition and the composition can be formulated and effectively applied for its intended purpose. By adhesive polymer what is meant is that when applied as a solution to a surface and dried, the polymer forms a film. Such a film will have adhesive and cohesive strength, as is understood by those skilled in the art.

The polysiloxane-grafted adhesive polymers are characterized by polysiloxane moieties covalently bonded to and pendant from a polymeric carbon-based backbone. The backbone will preferably be a carbon chain derived from polymerization of ethylenically unsaturated monomers, but can also be, cellulosic chains or other carbohydrate-derived polymeric chains to which polysiloxane moieties are pendant. The backbone can also include ether groups, e.g., C—O—C—. The polysiloxane moieties can be substituted on the polymer or can be made by co-polymerization of polysiloxane-containing polymerizable monomers (e.g. ethylenically unsaturated monomers, ethers, and/or epoxides) with non-polysiloxane-containing polymerizable monomers.

The polysiloxane-grafted polymer should have a weight average molecular weight of at least about 20,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 3,000,000. Preferably, the weight average molecular weight will be between about 50,000 and about 3,000,000, more preferably between about 75,000 and about 3,000,000, most preferably between about 750,000 and about 2,000,000.

Preferably, especially for personal care compositions, the grafted-polymers hereof when dried to form a film have a Tg or Tm of at least about −20° C., preferably at least about 20° C., so that they are not unduly sticky, or "tacky" to the touch. As used herein, the abbreviation "Tg" refers to the glass transition temperature of the non-polysiloxane backbone of the polymer, and the abbreviation "Tm" refers to the crystalline melting point of the non-siloxane backbone, if such a transition exists for a given polymer. Preferably, the Tm, if any, is also above about −20° C., more preferably above about 20° C.

The polysiloxane-grafted polymers for the compositions of the present invention are typically made by copolymerization of "silicone-containing" or "polysiloxane-containing" monomers with non-silicone-containing monomers. The polysiloxane-grafted polymers should satisfy the following four criteria:

(1) when dried the polymer phase-separates into a discontinuous phase which includes the polysiloxane portion and a continuous phase which includes the non-polysiloxane portion;

(2) the polysiloxane portion is covalently bonded to the non-polysiloxane portion; and (3) the molecular weight of the polysiloxane portion is at least about five hundred.

When used in a composition, such as a personal care composition for application to the hair or skin, the non-polysiloxane portion should permit the polymer to deposit on the intended surface, such as hair or skin.

It is believed that the phase separation property provides a specific orientation of the polymer which results in the desired combination of tactile feel, and film-forming or adhesive benefits. The phase-separating nature of the compositions of the present invention may be determined as follows:

The polymer is cast as a solid film out of a solvent (i.e., a solvent which dissolves both the backbone and the polysiloxane-graft portions). This film is then sectioned and examined by transmission electron micrography. Microphase separation is demonstrated by the observation of inclusions in the continuous phase. These inclusions should have the proper size to match the size of the silicone chain (typically a few hundred nm or less) and the proper density to match the amount of silicone present. This behavior is well documented in the literature for polymers with this structure (see, for example, S. D. Smith, Ph.D. Thesis, University of Virginia, 1987, and references cited therein.

A second method for determining phase-separating characteristics involves examining the enrichment of the concentration of silicone at the surface of a polymer film relative to the concentration in the bulk polymer. Since the silicone prefers the low energy air interface, it preferentially orients on the polymer surface. This produces a surface with the silicone oriented at the surface of the film. This can be demonstrated experimentally by ESCA (electron spectroscopy for chemical analysis) of the dried film surface. Such an analysis shows a high level of silicone and a greatly reduced level of backbone polymer when the film surface is analyzed. (Surface here means the first few tens of Angstroms of film thickness.) By varying the angle of the interrogating beam the surface can be analyzed to varying depths.

A third method for determining phase-separating characteristics is via Scanning Electron Microscopy (SEM), to examine the topographical morphology of dried film of the silicone grafted polymer. SEM can be used to demonstrate microphase separation at the surface of the polymer film by the observation of hemi-spherical discontinuities (typically hemi-spherical or hemi-conical) formed by the silicone macromer component grafted on the polymer backbone of the silicone grafted polymer.

The preferred polysiloxane-grafted polymers comprise an organic backbone preferably a carbon backbone derived from ethylenically unsaturated monomers, such as a vinyl polymeric backbone, and a polysiloxane macromer (especially preferred are polydialkylsiloxane, most preferably polydimethylsiloxane) grafted to the backbone. The polysiloxane macromer should have a weight average molecular weight of at least about 500, preferably from about 1,000 to about 100,000, more preferably from about 2,000 to about 50,000, most preferably about 5,000 to about 20,000. Organic backbones contemplated include those that are derived from polymerizable, ethylenically unsaturated monomers, including vinyl monomers, and other condensation monomers (e.g., those that polymerize to form polyamides and polyesters), ring-opening monomers (e.g., ethyl oxazoline and caprolactone), etc. Also contemplated are backbones based on cellulosic chains, ether-containing backbones, etc.

Examples of useful polymers and how they are made are described in detail in U.S. Pat. No. 4,693,935, Mazurek, issued Sep. 15, 1987, U.S. Pat. No. 4,728,571, Clemens et al., issued Mar. 1, 1988, both of which are incorporated herein by reference.

Suitable polysiloxane-grafted polymers are also disclosed in EPO Application 90307528.1, published as EPO Application 0 408 311 A2 on Jan. 11, 1991, Hayama, et al., U.S. Pat. No. 5,061,481, issued Oct. 29, 1991, Suzuki et al., U.S. Pat. No. 5,106,609, Bolich et al., issued Apr. 21, 1992, U.S. Pat. No. 5,100,658, Bolich et al., issued Mar. 31, 1992, U.S. Pat. No. 5,100,657, Ansher-Jackson, et al., issued Mar. 31, 1992, U.S. Pat. No. 5,104,646, Bolich et al., issued Apr. 14, 1992, and U.S. Ser. No. 07/758,319, Bolich et al, filed Aug. 27, 1991, and now abandoned, and the all of which are incorporated by reference herein.

The preferred polysiloxane grafted polymers are comprised of monomer units derived from: at least one free radically polymerizable ethylenically unsaturated monomer or monomers polysiloxane-containing, ethylenically unsaturated monomer or monomers.

The preferred polysiloxane grafted polymers hereof comprise from about 1% to about 50%, by weight, of polysiloxane-containing monomer units, i.e., monomer units polysiloxane-containing monomers, "C" monomers, and from about 50% to about 99% by weight, of non-polysiloxane-containing monomers. The non-polysiloxane-containing monomer units are generally derived from hydrophobic monomers, "A" monomers, or combination of A monomers and hydrophilic monomers, "B" monomers, and mixtures thereof.

Hydrophobic monomers means monomers which form substantially water insoluble homopolymers. Hydrophilic monomers means monomers which do not form substantially water insoluble homopolymers.

Substantially water soluble shall refer to monomers that form homopolymers that are soluble in distilled (or equivalent) water, at 25° C., at a concentration of 0.2% by weight, and are preferably soluble at 1.0% by weight. Substantially water insoluble shall refer to monomers that form homopolymers that are not soluble in distilled (or equivalent) water, at 25° C., at a concentration of 0.2% by weight, and preferably not soluble at 0.1% by weight. The weight average molecular weight for purposes of determining substantial water solubility or insolubility shall be about 100,000, although solubility at higher molecular weight will generally also be indicative of solubility at about 100,000.

Representative examples of A monomers are acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri methyl-1-hexanol, 1-decanol, 1-dodecanol, 1-hexadecanol, 1-octa decanol, and the like, the alcohols having from about 1–18 carbon atoms with the number of carbon atoms preferably being from about 1–12; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred A monomers include n-butyl methacrylate, isobutyl methacrylate, t-butyl acrylate, t-butyl methacrylate, 2-ethylhexyl methacrylate, methyl methacrylate, and mixtures thereof. Most preferably, A is selected from t-butyl acrylate, t-butyl methacrylate, and mixtures thereof.

Representative examples of B monomers include acrylic acid, methacrylic acid, N,N-dimethylacrylamide, dimethyl aminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (produced by the hydrolysis of vinyl acetate after polymerization), vinyl caprolactam, and mixtures thereof. Preferred B monomers include acrylic acid, N,N-dimethyl acrylamide, dimethylaminoethyl methacrylate, quaternized dimethyl aminoethyl methacrylate, vinyl pyrrolidone, salts of acids and amines listed above, and mixtures thereof.

Polymerizable polysiloxane-containing monomers (C monomer) are exemplified by the general formula:

$$X(Y)_n Si(R)_{3-m} Z_m$$

wherein X is an ethylenically unsaturated group copolymerizable with the A and B monomers, such as a vinyl group; Y is a divalent linking group; R is a hydrogen, hydroxyl, lower alkyl (e.g. $C_1$–$C_4$), aryl, alkaryl, alkoxy, or alkylamino; Z is a monovalent siloxane polymeric moiety having a number average molecular weight of at least about 500, is essentially unreactive under copolymerization conditions, and is pendant from the vinyl polymeric backbone described above; n is 0 or 1; and m is an integer from 1 to 3. C has a weight average molecular weight as described above. Preferably, the C monomer has a formula selected from the following group:

$$X-\overset{O}{\underset{\|}{C}}-O-(CH_2)_q-(O)_p-Si(R^1)_{3-m}Z_m$$

In this structure, m is 1, 2 or 3 (preferably m=1); p is 0 or 1; q is an integer from 2 to 6; $R^1$ is hydrogen, hydroxyl, lower alkyl, alkoxy, alkylamino, aryl, or alkaryl (preferably $R^1$ is alkyl); X is $$\underset{R^2\ \ R^3}{CH=C-}$$

$R^2$ is hydrogen or —COOH (preferably $R^2$ is hydrogen); $R^3$ is hydrogen, methyl or —$CH_2COOH$ (preferably $R^3$ is methyl); Z is $$R^4 + Si-O-)_r;\ \ \underset{R^6}{\overset{R^5}{|}}$$

$R^4$, $R^5$, and $R^6$ independently are lower alkyl, alkoxy, alkylamino, aryl, arkaryl, hydrogen or hydroxyl (preferably $R^4$, $R^5$, and $R^6$ are alkyls); and r is an integer of about 5 or higher, preferably about 10 to about 1500 (most preferably r is from about 100 to about 250). Most preferably, $R^4$, $R^5$, and $R^6$ are methyl, p=0, and q=3.

In general, the polysiloxane grafted polymer will preferably comprise from about 50% to about 99%, more preferably from about 60% to about 98%, most preferably from about 75% to about 95%, by weight of the polymer, of total A and B monomer units. The level of C monomer units is generally from about 1% to about 50%, preferably from about 1% to about 40%, more preferably from about 2% to about 25%. The composition of any particular polysiloxane grafted polymer will help determine its formulational properties. By appropriate selection and combination of particular A, B and C components, the adhesive agent polymer can be optimized for inclusion in specific vehicles. It is well within the skill of one in the art to select monomers for incorporation into the polymers for formulatability and solubility in a selected solvent The polymers preferably comprise from about 5% to about 99% (preferably from about 75% to about 90%) of monomer A, from 0 to about 60% (preferably from 0% to about 20%, most preferably from 0% to about 5% of monomer B, and from about 1% to about 40% (preferably from about 2% to about 25%) of monomer C.

The polysiloxane-grafted polymers can be synthesized by free radical polymerization of the polysiloxane-containing monomers with the non-polysiloxane-containing monomers. The general principles of free radical polymerization methods are well understood. See, for example, Odian, "Principles of Polymerization", 2nd edition, John Wiley & Sons, 1981, pp. 179–318. The desired monomers are all placed in a reactor, along with a sufficient amount of a mutual solvent so that when the reaction is complete the viscosity of the reaction is reasonable. Typical monomer loadings are from about 20% to about 50%. Undesired terminators, especially oxygen, are removed as needed. This is done by evacuation or by purging with an inert gas, such as argon or nitrogen. The initiator is introduced and the reaction brought to the temperature needed for initiation to occur, assuming thermal initiators are used. Alternatively, redox or radiation initiation can be used. The polymerization is allowed to proceed as long as needed for a high level of conversion to be achieved, typically from a few hours to a few days. The solvent is then removed, usually by evaporation or by precipitating the polymer by addition of a nonsolvent. The polymer can be further purified, as desired.

Volatile Solvent For The Polysiloxane-Grafted Polymer

The compositions of the present invention comprise a volatile, water insoluble liquid which is a solvent for the polysiloxane-grafted adhesive polymer.

In general, the present compositions will comprise from about 0.5% to about 99.8%. Preferably, for dispersions or emulsions the compositions will comprise from about 1% to about 25%, more preferably from about 2% to about 15%, most preferably from about 3% to about 12%, by weight of the composition, of the volatile solvent for the polysiloxane-grafted polymer.

As used herein, the term "volatile" refers to liquids having a boiling point at one atmosphere of 260° C. or less, preferably 250° C., more preferably 230° C. or less, most preferably 225° C. or less. In general, the boiling point of the volatile solvents will be at least about 50° C., preferably at least about 100° C. The term "nonvolatile", on the other hand, shall refer to materials which have a boiling point at one atmosphere of greater than 260° C. "Water insoluble solvent" refers to a solvent that is not miscible with water (distilled or equivalent) at 25° C.

The solvents hereof include silicone fluids, silane fluids, and organic oils such as hydrocarbons, esters, ethers, alcohols, and mixture,, thereof.

Especially preferred are volatile silicone fluids. Volatile silicone fluids suitable for use herein include both linear and cyclic silicone fluids. The viscosity of the volatile silicone fluids hereof will generally be about 10 cS or less at 25° C.

Volatile silicone fluids include polyalkylsiloxanes, polyalkylarylsiloxanes, and mixtures thereof.

Cyclic volatile silicone fluids include cyclopolysiloxanes such as cycloalkylsiloxanes and cycloalkylalkoxysiloxanes, wherein alkyl and alkoxy groups contain $C_1$–$C_8$ alkyl groups.

A general formula for cyclic volatile silicones contemplated for use herein is:

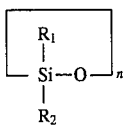

wherein n=3–7 and $R_1$ and $R_2$ are independently selected from $C_1$–$C_8$ alkyl, aryl (especially phenyl), and alkaryl (e.g., $C_1$–$C_8$ substituted aryl). Preferred are $R_1$ and $R_2$ being $C_1$–$C_2$ alkyl, most preferably $C_1$ and n=4–6. $R_1$ and $R_2$ can also be alkoxy, alkaryl, hydroxy, hydroxyalkyl, and derivatives thereof.

Specific examples include octomethyl cyclotetrasiloxane, decamethyl cyclopentasiloxane, methoxypropyl heptamethyl cyclotetrasiloxane, octomethyl cyclotetrasiloxane, and decamethyl cyclopentasiloxane. The volatile silicones in the compositions of the present invention are cyclic and linear polydimethylsiloxane. The number of silicone atoms in the preferred cyclic silicones is from about 3 to about 7, more preferably 4 or 5.

Linear volatile silicone fluids include polyorganosiloxanes such as polydialkylsiloxanes, polyalkylarylsiloxanes.

Examples of linear polyorganosiloxanes include those having from about 3 to about 9 silicon atoms are represented by the general formula:

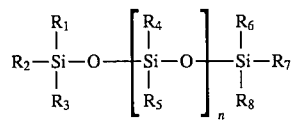

wherein $R_1$, $R_2$, $R_3$, $R_4$, $R_5$, $R_6$, $R_7$, and $R_8$ can independently be saturated or unsaturated $C_1$–$C_8$ alkyl, aryl, (preferably containing a $C_6$ aromatic ring), alkyl aryl, hydroxyalkyl, amino alkyl or alkyl siloxy, and n=1–7. The preferred volatile linear polydimethylsiloxanes have from about 3 to 9 silicone atoms and are polydialkylsiloxanes, especially those with $C_1$–$C_2$, preferably $C_1$, alkyls.

Examples of preferred linear materials include polydialkylsiloxanes such as polydimethylsiloxane having viscosity below about 10 cS at 25° C., and disiloxanes such as phenylpentamethyldisiloxane, chloropropyl pentamethyldisiloxane, and hydroxypropylpentamethyldisiloxane.

The linear volatile silicones generally have viscosities of 5 centistokes or less at 25° C., while the volatile cyclic materials generally have viscosities of 10 centistokes or less at 25° C. A description of volatile silicones is found in Todd and Byers, "Volatile Silicone Fluids for Cosmetics", Cosmetics and Toiletries, Vol. 91, January, 1976, pp. 27–32

Volatile silane liquids can also be used. Suitable silane compounds include those that have the general formula:

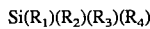

wherein $R_1$, $R_2$, $R_3$ and $R_4$ can independently be selected from $C_1$–$C_8$ alkyl, aryl, alkyl aryl, hydroxy alkyl and alkylsiloxy.

Other volatile solvents useful in the present compositions include hydrocarbons, esters, ethers, alkyl alcohols, and mixtures thereof. Preferred of these are the ester, ether, alkyl alcohol, and hydrocarbon fluids.

The hydrocarbons may be either straight or branched chain and may contain from about 10 to about 16, preferably from about 12 to about 16 carbon atoms. Examples of suitable straight chain hydrocarbons are decane, dodecane, decerie, tridecane and mixtures thereof. Suitable branched chain hydrocarbon solvents include $C_{10}$–$C_{16}$ branched chain hydrocarbons, and mixtures thereof, preferably $C_{11}$–$C_{14}$ branched chain hydrocarbons, more preferably $C_{12}$ branched chain hydrocarbons. Saturated hydrocarbons are preferred, although it isn't necessarily intended to exclude unsaturated hydrocarbons, Examples of such branched chain hydrocarbons include isoparaffins of the above chain sizes. Isoparaffins are commercially available from Exxon Chemical Co. Examples include Isopar™ and K($C_{11}$–$C_{12}$ isoparaffins), and Isopar™ L ($C_{11}$–$C_{13}$ isoparaffins). Another suitable branched chain hydrocarbon is isododecane. Isododecane is commercially available from Preperse, Inc. (South Plainfiled, N.J., USA) as Permethyl™ 99A. Also contemplated, though not preferred, are the terpenes such as orange and lemon terpenes.

Useful alkyl alcohols will typically contain from about 8 to about 12 carbon atoms and can be saturated or unsaturated, and have branched or straight chains. Suitable alkyl alcohols include, for example, linalool and decyl alcohol.

Useful esters include, for example, methyl alkanoates such as the $C_8$–$C_{12}$ alkanoates (e.g., methyl decanoate), di($C_2$–$C_3$)alkyl adipates (e.g., diethyl adipate, diisopropyl adipate), $C_6$–$C_{10}$ alkyl acetates (e.g., octyl acetate), and benzoates (e.g., butyl benzoate).

Useful ethers include di($C_5$–$C_7$) alkyl ethers, especially the di($C_5$–$C_6$) alkyl ethers such as dipentyl ether and dihexyl ether.

The preferred volatile solvents hereof are the silicone fluids, especially the cyclic silicone fluids, and $C_{10}$–$C_{16}$ branched chain hydrocarbons.

Drying Aid

The compositions of the present invention also comprise a nonvolatile drying aid for the polysiloxane-grafted polymer. The weight ratio of the polysiloxane-grafted polymer to the silicone resin should generally be about 100:1 or less, and will generally be from about 5:1 to about 100:1, preferably from about 5:1 to about 75:1, more preferably from about 7:1 to about 50:1, more preferably from about 10:1 to about 35:1, most preferably form about 12:1 to about 25:1. Higher ratios can be used as long as enhanced drying of the polysiloxane grafted polymer/volatile solvent solution is obtained. Lower ratios can be used as long as the drying aid remains soluble at 45° C. and does phase separate out of the volatile solvent/polysiloxane-grafted polymer phase of the composition.

The level of drying aid in the compositions hereof will preferably be from about 0.1% to about 2%, more preferably from about 2% to about 1.5%, most preferably from about 0.5% to about 1.5%, by weight of the volatile solvent for the polysiloxane-grafted polymer.

The drying aid should be water insoluble at 25° C. By "water insoluble", in reference to the drying aid, what is meant is that a 0.1% concentration of the drying aid is not soluble in distilled (or equivalent) water at 25° C. By "soluble" in the volatile solvent for the polysiloxane-grafted polymer, what is referred to is that the drying aid that is present in solubilized or miscible form at the indicated temperature, e.g. 45° C., in the solvent. "Nonvolatile" is as previously defined.

The drying aids hereof are, in general, silicon-containing materials. Suitable silicon-containing materials include silicone fluids, silicone resins, and silanes, and mixtures thereof.

Silicone resins are highly crosslinked polymeric siloxane systems. The crosslinking is introduced through the incorporation of trifunctional and tetrafunctional silanes with monofunctional or difunctional monomer units, or both, during manufacture of the silicone resin. As is well understood in the art, the degree of crosslinking that is required in order to result in a silicone resin will vary according to the specific silane units incorporated into the silicone resin. Silicone materials which have a sufficient level of trifunctional and tetrafunctional siloxane monomer units (and hence, a sufficient level of crosslinking) such that they dry down to a rigid film are silicone resins. The ratio of oxygen atoms to silicone atoms is indicative of the level of crosslinking in a particular silicone material. Silicone resins have at least about 1.1 oxygen atoms pr silicon atom. Preferably, the ratio of oxygen:silicone atoms is at least about 1.2:1.0.

Silicone resins are manufactured from silanes according to techniques well known in the art are widely available. Typical silanes used in the manufacture of silicone resins are monomethyl-, dimethyl-, monophenyl-, diphenyl-, methylphenyl-, monovinyl-, and methylvinylchlorosilanes, and tetrachlorosilane. Preferred silicone resins are the methyl substituted silicone resins, such as those offered by General Electric as GE SS4230 and SS 4267. Commercially available silicone resins will generally be supplied in an unhardened form in a low viscosity nonvolatile or, preferably, volatile silicone fluid. The silicone resins for use herein are preferably obtained and incorporated into the present compositions in such non-hardened form. However, hardened resin can also be used as long as it dissolves in the volatile solvent at 45° C.

Silicone resins are especially preferred for use in the present invention since they can increase style hold strength of hair in hair care compositions hereof, in addition to decreasing drying time.

Background material on silicones including sections discussing silicone fluids and resins can be found in *Encyclopedia of Polymer Science and Engineering,* Volume 15, Second Edition, pp 204–308, John Wiley & Sons, Inc. 1989, and Chemistry and Technology of Silicones, Walter Noll, Academic Press, Inc. (Harcourt Bruce Javanovich, Publishers, New York), 1968, pp 282–287 and 409–426, both incorporated herein by reference.

Silicone resins can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetrafunctional unit $SiO_2$. Primes of the unit symbols, e.g., M', D', T', and Q' denote substituents other than methyl., and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T'; and/or Q' to D, D' M and/or or M' in a silicone resin is indicative of higher levels of crosslinking. As discussed before, however, the overall level of crosslinking can also be indicated by the oxygen to silicone ratio.

The silicone resins for use herein which are preferred are MQ, MT, MTQ, MDT, and MDTQ resins. Thus, the preferred silicone substituent is methyl. Especially preferred are MQ resins particularly those wherein the M:Q molar ratio is from about 0.5:1.0 to about 1.5:1.0 and the average molecular weight of the resin is from about 1000 to about 10,000.

Another category of drying aids are the silicone fluids and waxes having from 1 to about 100 siloxy units. The "silicone fluids" generally will have a viscosity of 1,000,000 centistokes or less at 25° C., preferably about 100,000 cS or less, more preferably about 10,000 cS or less, even more preferably about 1,000 cS or less, most preferably about 100 cS or less. Viscosity will generally be at least about 5 cs, more generally be at least about 5 cS, more generally at least about 10 cS, at 25° C. Silcone wax refers to silicone compounds that are solids at 25° C., but do not have the requsite level of crosslinking required for a silicone resin, as described above. The purposes hereof, "solid" "shall mean that the material, when dried, does not exhibit a substantial amount of gravity induced flow over the time frame of one hour i.e., a sample of said material retains substantially the same geometry and proportions after a one hour period.

Suitable silicone fluids and waxes include polyalkyl siloxanes, polyaryl siloxanes, polyalkylaryl siloxanes, and mixtures thereof. Other insoluble, nonvolatile silicone fluids having hair conditioning properties can also be used.

More particularly silicone fluids and waxes hereof include polysiloxanes with the following structure:

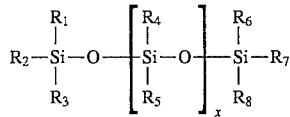

wherein $R_1$, $R_2$, $R_3$, $R_4$, $R_5$, $R_6$, $R_7$, and $R_8$ can independently be R is aliphatic, preferably alkyl or alkenyl, aryl, alkoxy, aryloxy, alkaryl, arylalkyl, arylalkenyl, alkamino, alkether, hydroxyalkyl, hydrooxy, or alkyl siloxy. The R groups can be further substituted, e.g. with halogens, cationic amines and quaternary ammonium groups, etc. The variable x is an integer from 1 to about 100. The silicone fluids and waxes hereof will preferably have "x" from 5 to about 80, more preferably from 10 to about 50.

The aliphatic or aryl groups substituted on the siloxane chain may have any structure as long as the resulting silicones are hydrophobic, are neither irritating, toxic nor otherwise harmful when applied to the body, hair, or other surface are compatible with the other components of the composition, and are chemically stable under normal use and storage conditions.

The two R groups on the silicon atom of each monomeric silicone unit may represent the same group or different groups. Preferably, the two R groups represent the same group.

Preferred aliphatic chains for the radicals $R_1$–$R_8$ hereof are $C_1$–$C_{24}$ alkyls and alkenyls. Silicone fluids will preferably have $C_1$–$C_4$, more preferably from $C_1$–$C_2$, most preferably $C^1$ aliphatic chains, especially alkyl. The aliphatic portions of other alkyl-, alkenyl-, or alkynyl-containing groups (such as alkoxy, alkaryl, and alkamino) can be straight or branched chains $C_1$–$C_{24}$ carbon atoms and preferably have from one to five carbon atoms, more preferably from one to four carbon atoms, even more preferably from one to three carbon atoms, most preferably from one to two carbon atoms. Silicone waxes will comprise one or more longer chain aliphatic radical e.g. $C_8$–$C_{24}$, preferably $C_{12}$–$C_{22}$, aliphatic chain e.g. alkyl or alkenyl. This also includes alkoxy, alkester, and other groups described herein containing long chain aliphatic portions. As discussed above, the R substituents hereof can also contain amino functionalities, e.g. alkamino groups, which can be primary, secondary or tertiary amines or quaternary ammonium. These include mono-, di- and tri- alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$-$C_3$ alkyl. Examples of such polysiloxanes include polymethyl-3,3,3 trifluoropropylsiloxane.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

Other suitable R groups include methyl, methoxy, ethoxy, propoxy, and aryloxy. The three R groups on the end caps of the silicone may also represent the same or different groups.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

Polysiloxanes such as exemploy silicone waxes include $C_{12}C_{22}$ alkyl methyl polysiloxanes, such as cetyl and stearyl dimethic, one, and behenoxy dimethicone. Examples include Abil-Wax 9800™, a stearyl dimethicone available from Goldschmidt, and Abil-Wax 9801™, a cetyl dimethicone, and Abil Wax 2440™ a behenoxy dimethicone.

Silanols and alkoxy silicone fluids hereof will generally have hydroxy and shod chain ($C_1$-$C_3$, preferably $C_1$) alkoxy terminating groups at one of the $R_1$, $R_2$, or $R_3$ substituents and at one of the $R_6$, $R_7$, and $R_8$ substituents.

Alkylamino substituted silicones that can be used herein include those of the formula:

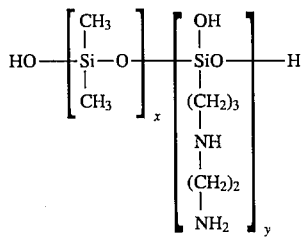

in which x and y are integers which depend on the molecular weight, the average molecular weight being approximately between 5,000 and 10,000. This polymer is also known as "amodimethicone".

Cationic silicone fluids which can be used in the present compositions include those that correspond to the formula:

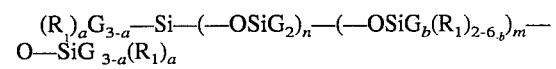

in which G is chosen from the group consisting of hydrogen, phenyl, OH, $C_1$-$C_8$ alkyl and preferably methyl; a denotes 0 or an integer from 1 to 3, and preferably equals 0;

b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R_1$ is a monovalent radical of formula $C_qH_{2q}L$ in which q is an integer from 2 to 8 and L is chosen from the groups

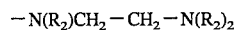

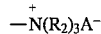

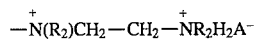

in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

An especially preferred cationic silicone corresponding to formula immediately above is the polymer known as "trimethylsilylamodimethicone", of formula:

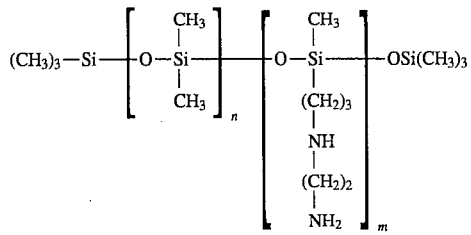

Other silicone cationic polymers which can be used in the present compositions correspond to the formula:

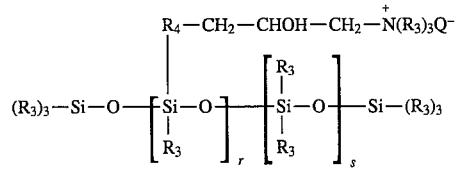

in which $R_3$ denotes a monovalent hydrocarbon radical having from 1 to 18 carbon atoms, and more especially an alkyl or alkenyl radical such as methyl;

$R_4$ denotes a hydrocarbon radical such as, preferably a $C_1$-$C_{18}$ alkylene radical or a $C_1$-$C_{18}$, and preferably $C_1$-$C_8$, alkyleneoxy radical; $Q^-$ is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017.

A polymer of this class which is especially preferred is that sold by UNION CARBIDE under the name "UCAR SILICONE ALE 56".

Nonvolatile silane liquids can also be used. Suitable silane compounds include those that have the general formula:

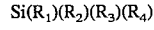

wherein $R_1$, $R_2$, $R_3$ and $R_4$ can independently be selected from $C_1$-$C_{20}$ alkyl, aryl, alkyl aryl, hydroxy alkyl and alkylsiloxy. Preferred silanes include $C_{10}$-$C_{18}$ alkoxy, $C_1$–$C_3$ alkyl (preferably $C_1$) silanes, such as stearoxy trimethyl silane.

Compositions

The compositions of the present invention will comprise from about 0.7% to 100%, by weight of the composition, of the polysiloxane-grafted polymer/drying aid/volatile solvent phase, preferably from about 0.1% to about 50%, more preferably from about 0.2% to about 30%, most preferably from about 0.2% to about 15%. The compositions preferably comprise from about 50% to about 99.3%, preferably from about 70% to about 99%, more preferably from about 85% to about 98%, of a carrier for the polymer/drying aid/solvent phase. Any carrier suitable for delivery of the polymer/resin/volatile solvent to the intended surface (such as the hair or skin) can be used. The carrier will comprise a volatile liquid which is water or is otherwise water soluble, or a mixture thereof and in which the volatile solvent of the polysiloxane-grafted polymer is not be soluble. In general, the compositions will comprise from about 50% to about 99.3%, preferably from about 70% to about 99%, more preferably from about 85% to about 98%, of such volatile carrier liquid.

The carrier liquid herein can include water and other hydrophilic fluids, and combinations thereof. Suitable carrier fluids for use in the present invention, in addition to water, include lower alcohols ($C_1$–$C_4$ alcohols, preferably $C_2$–$C_4$ alcohols such as ethanol and isopropanol) and mixtures of lower alcohols. Preferred solvents include water, ethanol, and mixtures thereof. Especially preferred is water.

The preferred compositions are in the form of a discontinuous phase of dispersed droplets, or particles, of the polysiloxane-grafted polymer/volatile solvent/drying aid distributed throughout the carrier. Such carrier can also comprise a variety of other components, such as other active ingredients, rheology modifiers such as thickeners, gelling agents, etc. The compositions of the present invention can be in the form of liquids, lotions, creams gels, etc. Furthermore the present compositions can be useful for a wide variety personal care products. These include, but are not limited to, hair care compositions such as hair rinses, shampoos, creams, gels, and lotions. The compositions hereof also include skin care compositions such as, but not limited to, make-up, mascara, foundations, sunscreens, skin conditioners, etc. The compositions are further useful as products formulated for delivery of active ingredients, such as medicaments, to or through the skin. In these latter formulations, the film-forming ability of the polymer can be utilized to entrap the active ingredient next to the skin.

The carrier may include gel vehicle materials or other rheology modifiers. These are particularly contemplated for use in products such as hair rinses, shampoos, mousses, and creams and lotions.

Gel vehicles can comprise two essential components: a lipid vehicle material and a cationic surfactant vehicle material. Cationic surfactant materials are described in detail below. Gel vehicles are generally described in the following documents: Barry, "The Self Bodying Action of the Mixed Emulsifier Sodium Dodecyl Sulfate/Cetyl Alcohol", 28 J. of Colloid and Interface Science 82–91 (1968); Barry, et al., "The Self-Bodying Action of Alkyltrimethylammonium Bromides/Cetostearyl Alcohol Mixed Emulsifiers; Influence of Quaternary Chain Length", 35 J. of Colloid and Interface Science 689–708 (1971); and Barry, et al., "Rheology of Systems Containing Cetomacrogol 1000—Cetostearyl Alcohol, I. Self Bodying Action", 38 J. of Colloid and Interface Science 616–625 (1972).

The carrier may incorporate one or more lipid vehicle materials, regardless of whether it also contains a cationic surfactant, which are essentially water-insoluble, and contain hydrophobic and hydrophilic moieties. Lipid vehicle materials include naturally or synthetically-derived acids, acid derivatives, alcohols, esters, ethers, ketones, and amides with carbon chains of from about 12 to about 22, preferably from about 16 to about 18, carbon atoms in length. Fatty alcohols and fatty esters are preferred; fatty alcohols are particularly preferred.

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Lipid vehicle materials among those useful herein are disclosed in *Bailey's Industrial Oil and Fat Products*, (3rd edition, D. Swern, ed., 1979). Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; and U.S. Pat. No. 4,269,824, Villamarin, et al., issued May 26, 1981. British Specification 1,532,585, published Nov. 15, 1978. and Fuku Shima, et al., "The Effect of Cetostearyl Alcohol in Cosmetic Emulsions", 98 *Cosmetics & Toiletries* 89–112 (1983) disclose additional fatty alcohols suitable for use herein. Fatty esters included among those useful herein are disclosed in U.S. Pat. No. 3,341,465, Kaufman, et al., issued Sep. 12, 1976 (incorporated by reference herein). If included in the compositions of the present invention, the lipid vehicle material is typically present at from about 0.1% to about 10.0% of the composition; the cationic surfactant vehicle material is present at from about 0.05% to about 5.0% of the composition.

The use of nonionic cellulose ethers and water-soluble gums for thickening compositions are also contemplated. See for example, U.S. Pat. No. 4,557,928, Glover, issued Dec. 10, 1985, teaching a hair conditioner comprising a suspension system which consists of one of glucan gum, guar gum, and hydroxyethylcellulose; and U.S. Pat. No. 4,581,230, Grollier et al., issued Apr. 8, 1986, which teaches cosmetic compositions for treating hair which comprise as thickening agents hydroxyethylcellulose, or water-soluble vegetable thickening agents, such as guar gum, each incorporated herein by reference.

Cellulose ethers are relatively low molecular weight but which are capable of producing highly viscous aqueous solutions in practical concentrations. These materials are nonionic cellulose ethers having a sufficient degree of nonionic substitution selected from the group consisting of methyl, hydroxyethyl, and hydroxypropyl to cause them to be water-soluble and which are further substituted with a hydrocarbon radical having from about 10 to 24 carbon atoms in an amount between about 0.2 weight percent and the amount which renders said cellulose ether less than 1%, by weight, soluble in water. The cellulose ether to be modified is preferably one of low to medium molecular weight; i.e., less than about 800,000 and preferably between about 20,000 and 700,000 (about 75 to 2500 D.P.).

Nonionic water-soluble cellulose ethers are preferred polymers that can be employed in hair care compositions. Widely used, commercially-available nonionic cellulose ethers include methyl cellulose, hydroxy propyl methyl cellulose, hydroxyethyl cellulose, hydroxypropyl cellulose and ethyl hydroxyethyl cellulose.

Other carrier ingredients for use in the compositions of the present invention, especially for hair rinses, include combinations of hydrophobically-modified polymeric materials with surfactants, such as quaternary ammonium compounds (such as ditallowdimethyl ammonium chloride). These vehicles are described in detail in the following patents: U.S. Pat. No. 5,106,609, issued Apr. 21, 1992 to Bolich et al., U.S. Pat. No. 5,100,658, issued Mar. 31, 1992 to Bolich et al., U.S. Pat. No. 5,104,646, issued Apr. 14, 1992 to Bolich et al, and U.S. Pat. No. 5,100,657, issued Mar. 31, 1992 to Ansher-Jackson et al., each incorporated herein by reference.

It is also contemplated to utilize a suspending agent to thicken the compositions and/or suspend the polymer/resin/solvent phase. Suitable suspending agents are long chain acyl derivatives, long chain amine oxides, and mixtures thereof, wherein such suspending agents are present in the shampoo compositions in crystalline form. A variety of such suspending agents are described in U.S. Pat. No. 4,741,855, Grote et al., issued May 3, 1988. Especially preferred is ethylene glycol distearate.

Also included among the long chain acyl derivatives useful as suspending agents are the N,N-di(hydrogenated) $C_8$–$C_{22}$ (preferably $C_{12}$–$C_{22}$, more preferably $C_{16}$–$C_{18}$) amido benzoic acid, or soluble salt (e.g., K, Na salts) thereof particularly N,N-di(hydrogenated)tallow amido benzoic acid which is commercially marketed by Stepan Company (Northfiled, Ill., USA).

These systems provide a gel-like rheology without necessarily being gels in the technical sense. By "hydrophobically modified nonionic water-soluble polymer" is meant a nonionic water-soluble polymer which has been modified by the substitution with a sufficient amount of hydrophobic groups to make the polymer less soluble in water. By "water-soluble" what is meant is the polymer or salt, thereof, constituting the polymer backbone of the thickener should be sufficiently soluble such that it forms a substantially clear solution when dissolved in water at a level of 1%, by weight of the solution, at 25° C. Hence, the polymer backbone of the primary thickener can be essentially any water-soluble polymer. The hydrophobic groups can be $C_8$ to $C_{22}$ alkyl, aryl alkyl, alkyl aryl groups and mixtures thereof. The degree of hydrophobic substitution on the polymer backbone should be from about 0.10% to about 1.0%, depending on the particular polymer backbone. More generally, the ratio of hydrophilic portion to hydrophobic portion of the polymer is from about 10:1 to about 1000:1.

Nonionic water-soluble cellulose ethers are preferred to be employed as the polymer substrate of these hydrophobically modified polymers. Thus, e.g., hydroxyethyl cellulose, hydroxypropyl cellulose, methyl cellulose, hydroxypropyl methyl cellulose, ethyl hydroxyethyl cellulose, and methyl hydroxyethyl cellulose can all be modified. The amount of nonionic substituent such as methyl, hydroxyethyl or hydroxypropyl is taught not to be critical so long as there is an amount sufficient to assure that the ether is water-soluble.

The long chain alkyl modifier can be attached to the cellulose ether substrate via an ether, ester or urethane linkage. The ether linkage is preferred.

One commercially available material which meets these requirements is NATROSOL PLUS Grade 430, hydrophobically modified hydroxyethylcellulose available from Aqualon Company, Wilmington, Del. This material has a $C_{16}$ alkyl substitution of about 0.5% to about 0.9% by weight. The hydroxyethyl molar substitution for this material is from about 2.8 to about 3.2. The average molecular weight for the water-soluble cellulose prior to modification is approximately 300,000.

Another material of this type is sold under the trade name NATROSOL PLUS CS Grade D-67, by Aqualon Company, Wilmington, Del. This material has a $C_{16}$ alkyl substitution of from about 0.50% to about 0.95%, by weight. The hydroxyethyl molar substitution for this material is from about 2.3 to about 3.3. The average molecular weight for the water-soluble cellulose prior to modification is approximately 700,000.

Examples of water soluble polymers include hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone, dextrans, for example Dextran purified crude Grade 2P, available from D&O Chemicals, plant exudates such as acacia, ghatti, and tragacanth, seaweed extracts such as sodium alginate, propylene glycol alginate, sodium carrageenan, cationic polymers such as Ucare JR-polymer (a cationic modified hydroxyethyl cellulose available from Union Carbide), natural polysaccharide materials, such as guar gum, locust bean gum, and xanthan gum.

When such systems are used to thicken the present compositions, from about 0.3% to about 5.0%, preferably from about 0.4% to about 3.0%, of the hydrophobically modified nonionic polymer is preferably utilized with from about 0.3% to about 5.0%, preferably from about 0.4% to about 3.0%, of the water-soluble polymeric material.

An alternative secondary thickening material for the hydrophobically modified nonionic polymer is a water-soluble surfactant having a molecular weight of less than about 20,000. By "water-soluble surfactant≤" is meant surfactant materials which form substantially clear, isotropic solutions when dissolved in water at 0.2 weight percent at 25° C.

Essentially any water-soluble surfactant material which meets these requirements will work in the present invention. However, the following materials have been found to be particularly preferred: cetyl betaine, ammonium lauryl sulfate, ammonium laureth sulfate, cetyl trimethyl ammonium chloride, and mixtures thereof.

When such systems are used to thicken the present compositions, from about 0.1% to about 10.0%, preferably from about 0.2% to about 5.0%, of the hydrophobically-modified nonionic water soluble polymer is generally utilized with from about 0.02% to about 0.30%, preferably from about 0.05% to about 0.30%, most preferably from about 0.05% to about 0.20%, of the water-soluble surfactant. The water-soluble surfactant level is kept low because higher levels of water-soluble surfactants interfere with the hydrophobically-modified hydroxyethyl cellulose thickener and produce compositions with much less desirable rheologies.

When the hydrophobically-modified polymer is combined with is a water-insoluble surfactant having a molecular weight of less than about 20,000. By "water-insoluble surfactant" is meant surfactant materials which do not form substantially clear isotropic solutions when dissolved in water at greater than 0.2 weight percent at 25° C.

Essentially any water-insoluble surfactant material which meets these requirements will work in the present invention, however, water-insoluble cationic surfactant materials are preferred. Cationic surfactants are described below. The following nonexclusive materials are suitable: stearamide diethanolamine (stearamide DEA), cocoamide methanolamine (cocoamide MEA), dimethyl stearamine oxide, glyceryl monooleate, sucrose stearate, PEG-2 stearamine, polyethylene glycol ethers of fatty alcohols, such as Ceteth-2 of the formula $CH_3$—$(CH2)$–$CH2$-$(OCH2CH2)_n$—$OH$, where n has an average value of 2 (commercially available under the trade name Brij 56 from ICI Americas), glycerol stearate citrate, dihydrogenated tallow dimethyl ammonium chloride, polyoxyethylene, polyoxypropylene block polymers such as Poloxamer 181, of the formula:

HO—(CH2—CH2—O)$_x$(CH—CH2—O)$_y$(CH2—CH2O)$_z$H;

wherein on average x=3, y=30 and z=3 (commercially available from BASF Wyandotte under the trade name Pluronic L-61), hydrogenated tallow dimethyl betaine, and hydrogenated tallow amide DEA.

When such systems are used to thicken the present compositions, from about 0.1% to about 10.0%, preferably from about 0.2% to about 5.0%, of the hydrophobically-modified hydroxyethyl cellulose is generally utilized with from about 0.02% to about 10.0%, preferably from about 0.05% to about 3.0%, most preferably from about 0.05% to about 2.0%, of the water-insoluble surfactant.

Cationic surfactants useful in the compositions of the present invention, including the gel vehicle systems as well as hydrophobically modified cellulose vehicle systems, contain amino or quaternary ammonium hydrophilic moieties which are positively charged when dissolved in the aqueous composition of the present invention. Cationic surfactants among those useful herein are disclosed in the following documents, all
Surfactants Surfactants are optional ingredients in the compositions of the invention, particularly shampoo and conditioner compositions. When present, the surfactant typically comprises from about 0.05% to about 50% of the composition. For a shampoo, the level is preferably from about 10% to about 30%, most preferably from about 12% to about 25%, of the composition. For conditioners, the preferred level of surfactant is from about 0.2% to about 3%. Surfactants useful in compositions of the present invention include anionic, nonionic, cationic, zwitterionic and amphoteric surfactants.

Synthetic anionic detergents useful herein, particularly for shampoo compositions, include alkyl and alkyl ether sulfates. These materials typically have the respective formulae ROSO$_3$M and RO(C$_2$H$_4$O)xSO$_3$M, wherein R is alkyl or alkenyl of from about 10 to about 20 carbon atoms, x is 1 to 10, and M is a water-soluble cation such as ammonium, sodium, potassium and triethanolamine. Another suitable class of anionic surfactants are the water-soluble salts of the organic, sulfuric acid reaction products of the general formula:

R$_1$—SO$_3$—M wherein R$_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., SO$_3$, H$_2$SO$_4$, oleum, obtained according to known sulfonation methods, including bleaching and hydrolysis. Preferred are alkali metal and ammonium sulfonated C$_{12-18}$ n-paraffins.

Additional examples of anionic synthetic surfactants which come within the terms of the present invention are the reaction products of fatty acids estertried with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278.

Still other anionic synthetic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuc cinicacid; dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkane-sulfonates. The α-olefins from which the olefin sulfonates are derived are mono-olefins having about 12 to about 24 carbon atoms, preferably about 14 to about 16 carbon atoms. Another class of anionic organic surfactants are the β-alkyloxy alkane sulfonates. These compounds have the following formula:

$$R_1-\underset{\underset{H}{|}}{\overset{\overset{OR_2}{|}}{C}}-\underset{\underset{H}{|}}{\overset{\overset{H}{|}}{C}}-SO_3M$$

where R$_1$ is a straight chain alkyl group having from about 6 to about 20 carbon atoms, R$_2$ is a lower alkyl group having from about 1 (preferred) to about 3 carbon atoms, and M is a water-soluble cation as hereinbefore described.

Many additional nonsoap synthetic anionic surfactants are described in *McCutcheon's, Detergents and Emulsifiers*, 1984 *Annual,* published by Allured Publishing Corporation. Also U.S. Pat. No. 3,929,678, Laughlin et al., issued Dec. 30, 1975, discloses many other anionic as well as other surfactant types and is incorporated herein by reference.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. Those derived from the condensation of ethylene oxide with the product resulting from the reaction of propylene oxide and ethylene diamine products.
2. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.
3. Long chain tertiary amine oxides such as those corresponding to the following general formula:

R$_1$R$_2$R$_3$N→O wherein R$_1$ contains an alkyl, alkenyl or monohydroxy alkyl radical of from about 8 to about 18 carbon atoms, from 0 to about 10 ethylene oxide moieties, and from 0 to about 1 glyceryl moiety, and R$_2$ and R$_3$ contain from about 1 to about 3 carbon atoms and from 0 to about 1 hydroxy group, e.g., methyl, ethyl, propyl, hydroxyethyl, or hydroxypropyl radicals (the arrow in the formula is a conventional representation of a semipolar bond).

4. Long chain tertiary phosphine oxides corresponding to the following general formula:

RR'R''P→O wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R'' are each alkyl or monohydroxyalkyl groups containing from about 1 to about 3 carbon atoms. The arrow in the formula is a conventional representation of a semipolar bond.

5. Long chain dialkyl sulfoxides containing one shod chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetra decyl methyl sulfoxide, 3-methoxytridecyl methyl sulfoxide, 3-hydroxytridecyl methyl sulfoxide, 3-hydroxy-4-dodecoxybutyl methyl sulfoxide.

Cationic surfactants useful in compositions of the present invention, particularly the conditioner compositions, contain amino or quaternary ammonium hydrophilic moieties which are positively charged when dissolved in the aqueous composition of the present invention. Cationic surfactants among those useful herein are disclosed in the following documents, all incorporated by reference herein: M. C. Publishing Co., *McCutcheon's, Detergents & Emulsifiers*, (North American edition 1979); Schwartz, et al., *Surface Active Agents, Their Chemistry and Technology*, New York: Interscience Publishers, 1949; U.S. Pat. No. 3,155,591 Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983, which patents are incorporated by reference. If included in the compositions of the present invention, the cationic surfactant is present at from about 0.05% to about 5%.

Among the quaternary ammonium-containing cationic surfactant materials useful herein are those of the general formula:

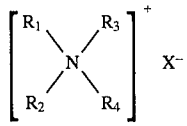

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups. The longer chain aliphatic groups, eg., those of about 12 carbons, or higher, can be saturated or unsaturated.

Other quaternary ammonium salts useful herein are diquaternary ammonium salts, such as tallow propane diammonium dichloride.

Quaternary ammonium salts include dialkyldimethyl-ammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride ditallowdimethyl ammonium methyl sulfate, dihexadecyl dimethyl ammonium chloride, di(hydrogenated tallow) dimethyl ammonium chloride, dioctadecyl dimethyl ammonium chloride, dieocosyol dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(saturated or unsaturated tallow) dimethyl ammonium chloride is a particularly preferred quaternary ammonium salt.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

Zwitterionic surfactants, useful in shampoos as well as conditioners, are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. A general formula for these compounds is:

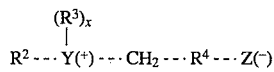

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionics such as betaines are also useful in the present invention. Examples of betaines useful herein include the high alkyl betaines, such as coco dimethyl carboxymethyl betaine, lauryl dimethyl carboxymethyl betaine, lauryl dimethyl alpha carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH(CH$_2$)$_3$ radical is attached to the nitrogen atom of the betaine are also useful in this invention.

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylamino propane sulfonate, Nalkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Silicone Hair Conditioning Agent

An optional component of the present invention is a nonvolatile, silicone conditioning agent which is not intermixed in the same phase as the volatile solvent of the polysiloxane-grafted copolymer.

The silicone hair conditioning agent for use herein will preferably have an average viscosity of from about 1,000 to about 2,000,000 centistokes at 25° C., more preferably from about 10,000 to about 1,800,000, even more preferably from about 100,000 to about 1,500,000. The viscosity of silicones herein can, in general, be measured by means of a glass capillary viscometer as set forth in Dow Corning Corporate Test Method CTM0004, Jul. 20, 1970.

The silicone hair conditioning agent will typically be used in the shampoo compositions hereof at levels of from about .05% to about 10% by weight of the composition, preferably from about 0.1% to about 10%, more preferably from about 0.5% to about 8%, most preferably from about 0.5% to about 5%.

Suitable insoluble, nonvolatile silicone fluids include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used. The term "nonvolatile" as used herein shall mean that the silicone material exhibits very low or no significant vapor pressure at ambient conditions, as is understood by those in the art. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000.

Silicone fluids hereof also include polyalkyl or polyaryl siloxanes with the following structure:

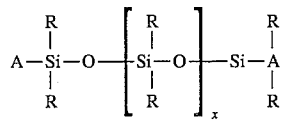

wherein R is alkyl or aryl, and x is an integer from about 1 to about 8,000 may be used, preferably from about 5 to about 8,000. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

The nonvolatile polyalkylsiloxane fluids that may be used include, for example, polydimethylsiloxanes. These siloxanes are available, for example, from the General Electric Company in their Viscasil$^R$ and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979, which patent is incorporated by reference, and Noll, Walter, Chemistry and Technology of Silicones, New York: Academic Press 1968. Also describing silicone gums are General Electric Silicone Rubber Product Data Sheets SE 30, SE 33, SE 54 and SE 76. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Cationic Polymer Hair Conditioning Agent

The compositions of the present invention can also comprise a water soluble, cationic organic polymer conditioning agent for hair or skin. The polymeric cationic conditioning agent hereof will generally be present at levels of from about 0.05% to about 5%, preferably from about 0.1% to about 4%, more preferably from about 0.2% to about 3%, by weight, of the shampoo composition. By "water soluble" cationic organic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration.

The cationic organic polymers useful in the hair conditioning agent hereof are organic polymers that can provide conditioning benefits to hair and that are soluble in the shampoo composition. Any cationic polymers which can provide these benefits can be used. As used herein, the term "polymer" shall include materials whether made by polymerization of one type of monomer or made by two (i.e., copolymers) or more types of monomers.

The cationic polymers hereof will generally have a weight average molecular weight which is at least about 5,000, typically at least about 10,000, and is less than about 10 million. Preferably, the molecular weight is from about 100,000 to about 2 million. The cationic polymers will have cationic nitrogen-containing moieties such as quaternary ammonium or cationic amino moieties, or a mixture thereof.

The cationic charge density is preferably at least about 0.9 meq/gram, more preferably at least about 1.0 meq/gram, even more preferably at least about 1.1 meq/gram, most preferably at least about 1.2 meq/gram. The cationic charge density is preferably no greater than about 4 meq/gram, more preferably no greater than about 3.0 meq/gram, most preferably no greater than about 2.0 meq/gram. Cationic charge density of the cationic polymer can be determined according to the Kjeldahl Method. Those skilled in the art will recognize that the charge density of amino-containing polymers may vary depending upon pH and the isoelectric point of the amino groups. The charge density should be within the above limits at the pH of intended use, which will in general be from about pH 3 to about pH 9, most generally from about pH 4 to about pH 8.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a shod chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

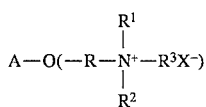

wherein:

A is an anhydroglucose residual group, such as a starch or cellulose anhydroglucose residual, $R^1$, $R^2$, $R^3$ is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer $JR^R$ and $LR^R$ series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., USA) under the tradename Polymer LM-200.

Other cationic polymers that can be used include cationic guar gum derivatives, such as guar hydroxypropyltrimonium chloride (commercially available from Celanese Corp. in their $Jaguar^R$ series). Other materials include quaternary nitrogen-containing cellulose ethers (e.g., as described in U.S. Pat. No. 3,962,418, incorporated by reference herein) and copolymers of etherified cellulose and starch (e.g., as described in U.S. Pat. No. 3,958,581, incorporated by reference herein).

Organic Oil Conditioning Agents

The compositions of the present invention can also comprise a nonvolatile, water insoluble, organic, oil as a conditioning agent for hair or skin. The hair conditioning oily liquid can add shine and luster to the hair. The conditioning oil is typically present in the compositions at a level of from about 0.05% to about 5%, by weight of the composition, preferably from about 0.2% to about 3%, more preferably from about 0.5% to about 1%.

By "nonvolatile" what is meant is that the oily material exhibits very low or no significant vapor pressure at ambient conditions (e.g., 1 atmosphere, 25° C.), as is understood in the art. The nonvolatile oily materials preferably have a boiling point at ambient pressure of about 250° C. or higher.

By "water insoluble" what is meant is that the oily liquid is not soluble in water (distilled or equivalent) at a concentration of 0.1%, at 25° C.

The conditioning oil hereof generally will have a viscosity of about 3 million cs or less, preferably about 2 million cs or less, more preferably about 1.5 million cs or less.

The conditioning oils hereof are liquids selected from the group consisting of hydrocarbon oils and fatty esters. The fatty esters hereof are characterized by having at least 10 carbon atoms, and include esters with hydrocarbyl chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 19 carbon atoms, although it is not necessarily meant to be limit the hydrocarbons to this range. Branched chain hydrocarbon oils can and typically may contain higher numbers of carbon atoms. Also encompassed herein are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 500, preferably from about 200 to about 400, more preferably from about 300 to about 350. Specific examples of suitable materials include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation. A preferred hydrocarbon polymer is polybutene, such as the copolymer of isobutylene and butene. A commercially available material of this type is L-14 polybutene from Amoco Chemical Co. (Chicago, Ill., U.S.A.).

Monocarboxylic acid esters hereof inlude esters of alcohols and/or acids of the formula R'COOR wherein alkyl or alkenyl radicals and the sum of carbon atoms in R' and R is at least 10, preferably at least 20.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

The mono-carboxylic acid ester however need not necessarily contain at least one chain with at least 10 carbon atoms, so long as the total number of aliphatic chain carbon atoms is at least 10. Examples include diisopropyl adipate, diisohexyl adipate, and diisopropyl sebacate.

Di- and tri-alkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Specific examples include isocetyl stearoyl stearate, diisopropyl adipate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

Glycerides include mono-, di-, and tri-glycerides. More specifically, included are the mono-, di-, and tri-esters of glycerol and long chain carboxylic acids, such as $C_{10}$–$C_{22}$ carboxylic acids, A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include triolein and tristearin glyceryl dilaurate. Preferred glycerides are di-, and tri-glycerides. Especially preferred are triglycerides.

The compositions herein can contain a variety of other optional components suitable for rendering such compositions more cosmetically or aesthetically acceptable or to provide them with additional usage benefits, e.g. medicinal benefits. Such conventional optional ingredients are well-known to those skilled in the art, e.g., sunscreens, medicaments (e.g. anti-bacterials, anti-inflamatories, anti-acne actives, etc.), colors and dyes, perfumes, peadescent aids, such as ethylene glycol distearate; preservatives, such as benzyl alcohol, methyl paraben, propyl paraben and imidazolidinyl urea; thickeners and viscosity modifiers, such as a diethanolamide of a long chain fatty acid (e.g., PEG 3 lauric diethanolamide), cocomonoethanol amide, dimethicone copolyols, guar gum, methyl cellulose, starches and starch derivatives; fatty alcohols, such as cetearyl alcohol; sodium chloride; sodium sulfate; polyvinyl alcohol; ethyl alcohol; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents, such as the thioglycolates; perfumes; sequestering agents, such as disodium ethylenediamine tetraacetate; and polymer plasticizing agents, such as glycerin, disobutyl adipate, butyl stearate, and propylene glycol. Such optional ingredients generally are used individually at levels of from about 0.01% to about 10.0%, preferably from about 0.05% to about 5.0%, of the composition.

The pH of the present compositions generally will be between about 3 and about 9, preferably between about 4 and about 8.

As with all compositions, the present invention should not contain components which unduly interfere with the performance of the compositions.

The cosmetic compositions of the present invention can be made using conventional formulation and mixing techniques. Methods of making various types of cosmetic compositions are described more specifically in the following examples.

Method of Use

The compositions of the present invention can be used in conventional manner to provide the adhesive and film-forming benefits of the present invention. Such method of use depends upon the type of composition employed but generally involves application of an effective amount of the product to the hair, skin, or nails, which may then be rinsed away (as in the case of shampoos and some hair rinse products) or allowed to remain on the hair (as in the case of leave-on products) or skin (for film-forming skin lotions such as medicaments, sunscreens, and cosmetics), or nails (e.g. nail polish). By "effective amount" is meant an amount sufficient to provide the adhesive benefits desired. Typically from about 0.1 to about 10 g of product is applied per square centimeter of surface, or about 1 g to about 40 g is applied to the hair. Preferably, hair rinse, mousse, and gel products are applied to wet or damp hair prior to drying and styling of the hair. Alternately, they can be applied to dry hair. After such compositions are applied to the hair, the hair is dried (if applicable) and styled in the usual ways of the user. Cosmetics and skin lotions are applied to face, skin, nails, or eye area in the conventional manners of usage for those types of products, and are then dried.

In the preferred methods hereof, the composition of the present invention is dried at elevated temperature, such as with the aid of a curling iron for the hair or with heated, forced air (e.g., a hair or "blow" dryer), at temperatures of about 45° C. or higher, preferably about 50° C. or 0 higher. The upper limit on temperature is governed primarily by safety and/or comfort to the user. However, elevated temperatures of 60°– 70° C., or higher are contemplated. When such high temperatures are used directly on skin or the hair, it will typically be for short durations (e.g., 10 seconds or less) so as to avoid discomfort or burns.

The following examples further illustrate preferred embodiments within the scope of the present invention. The examples are given solely for the purposes of illustration and are not to be construed as limitations of the present invention as many variations of the invention are possible without departing from its spirit and scope.

EXAMPLES I–III

The following are hair styling/conditioning rinse compositions representative of the present invention.

| Composition | I | II | III |
|---|---|---|---|
| Conditioner Premix | | | |
| DRO Water | q.s. | q.s. | q.s. |
| Citric Acid | 0.02 | 0.02 | 0.02 |
| Sodium Citrate | 0.09 | 0.09 | 0.10 |
| Cetyl Alcohol | 0.12 | 0.12 | 0.12 |
| Stearyl Alcohol | 0.08 | 0.08 | 0.08 |
| Natrosol Plus CS Grade D-67[1] | 1.02 | 1.00 | 0.99 |
| Xanthan Gum[2] | 0.25 | 0.25 | 0.25 |
| Styling Polymer Premix | | | |
| Polysiloxane-Grafted Polymer[7] | 1.75 | 1.75 | 1.75 |
| Octamethyl cyclotetrasiloxane | 5.98 | 5.98 | 5.98 |
| Decamethyl cyclopentasiloxane | 2.56 | 2.56 | 2.56 |
| Butyl Stearate | 0.15 | 0.15 | 0.15 |
| Trimethylsiloxysilicate | 0.11 | 0.11 | 0.11 |
| Kathon CG | 0.03 | 0.03 | 0.03 |
| Perfume | 0.33 | 0.33 | 0.33 |
| Silicone Premix | | | |
| DRO Water | 9.48 | 9.48 | 8.57 |
| Adogen 470[4] | 0.70 | 0.60 | 0.93 |
| Adogen 471[5] | 0.05 | 0.15 | 0.07 |
| Decamethyl cyclopentasiloxane/ Polydimethyl Siloxane Gum[3] | 1.67 | 1.67 | 2.33 |
| Amodimethicone (Dow Corning Q2-8220)[6] | 0.10 | 0.10 | 0.10 |

-continued

| Composition | I | II | III |
|---|---|---|---|
| Surfactant Premix | | | |
| DRO Water | 5.70 | 5.70 | 5.70 |
| Stearalkonium Chloride | 0.30 | 0.30 | 0.30 |

[1]Hydrophobically modified hydroxyethyl cellulose from Aqualon Corp.
[2]Readily dispersible xantham gum
[3]SE-76 gum available From General Electric
[4]Ditallow dimethyl ammonium chloride, Sherex Chemical Co., Dublin, Ohio, USA; 75% aqueous solution
[5]Tallow trimethyl ammonium chloride, Sherex Chemical Co.; 50% aqueous solution.
[6]Trimethylsilylamodimethicone
[7]80 wt % t-butyl acrylate/20 wt % silicone macromer (wt average molecular weight of 10,000), polymer weight average molecular weight of about 1,000,000

The styling polymer premix is prepared by combining the polymer, the octamethyl tetrasiloxane and decamethyl pentasiloxane, butyl stearate, and silicone resin.

The silicone premix is prepared by combining and mixing (in a separate vessel) water, Adogen 470 and Adogen 471 at 85° C. Cool to 71° C. and add the silicone gum/decamethyl cyclopentasiloxane solution and Amodimethicone and mix until homogeneous. Cool to 38° C. while using homogenizer (such as Tekmar).

The surfactant premix is prepared by combining and mixing (in a separate vessel) water and Stearalkonium Chloride at 38° C.

The conditioner premix is prepared by combining and mixing (in a separate vessel) the DRO water heated to 71° C. Citric acid, sodium citrate, cetyl alcohol, stearyl alcohol and Natrosol Plus CS grade D-67 are added and mixed until homogeneous. The xanthan gum is added and mixed until homogeneous. The styling polymer premix, Kathon CG and perfume are added and mixed until homogeneous. The composition is further dispersed with an in-line homogenizer (such as Tekmar homogenizer) and then cooled to 38° C.

The conditioner is completed by combining and mixing (in a separate vessel) the conditioner premix, the silicone premix and the surfactant premix at 38° C. This mixture is then cooled to 38° C.

When the compositions defined in Examples I–III are applied to hair in the conventional manner, they provide effective hair conditioning and styling/hold benefits without leaving the hair with a sticky/stiff feel.

EXAMPLE IV

Polymer Premix with added Drying Aid

Prepare the following premix utilizing conventional mixing techniques.

| Ingredients | Weight % |
|---|---|
| Polysiloxane-Grafted Polymer[1] | 16.83 |
| Octamethyl cyclotetrasiloxane | 69.30 |
| Decamethyl cyclopentasiloxane | 29.70 |
| Trimethylsiloxysilicate[1] | 1.00 |

[1]As in Example I.

This mix is prepared by adding the polysiloxane-grafted polymer to the solvents while mixing. Heat to 80°–84° C. in a covered vessel, maintaining mixing. Cool to 23°–27° C. and add trimethylsiloxysilicate while mixing.

EXAMPLE V

Polymer Premix with added Drying Aid

Prepare the following premix utilizing conventional mixing techniques.

| Ingredients | Weight % |
|---|---|
| Polysiloxane-Grafted Polymer[1] | 15.00 |
| Isododecane | 83.50 |
| Polydimethylsiloxane[2] | 1.50 |

[1]75 wt. % t-butylacrylate/5 wt. % acrylic acid/20 wt. % silicone macromer (10,000 MW), polymer weight average molecular weight of about 800,000
[2]Polydimethylsiloxane, Dow Corning, Dow Corning 200 Fluid (20 csk)

This mix is prepared by adding the polysiloxane-grafted polymer to the solvent while mixing. Heat to 80°–84° C. in a covered vessel, maintaining mixing. Cool to 23°–27° C. and add polydimethylsiloxane while mixing.

EXAMPLE VI

Polymer Premix with added Drying Aid

Prepare the following premix utilizing conventional mixing techniques.

| Ingredients | Weight % |
|---|---|
| Polysiloxane-Grafted Polymer[2] | 20.00 |
| Linalool | 79.50 |
| Cetyl Dimethicone | 0.50 |

[1]Cetyl Dimethicone, Goldschmidt, Abil Wax 9800
[2]75 wt. % t-Butyl Acrylate/5 wt. % Dimethyl Acylamide/20 wt. % Silicone Macromer (10,000 MW), polymer wt. ave. MW of 600,000

This mix is prepared by adding the polysiloxane-grafted polymer to the solvent while mixing. Heat to 80°–84° C. in a covered vessel, maintaining mixing. Add the cetyl dimethicone and cool to 23°–27° C. while mixing.

EXAMPLE VII

Mousse

Mousse compositions are prepared from the following components utilizing conventional mixing techniques.

| | Weight % | | |
|---|---|---|---|
| Ingredients | A | B | C |
| Water | QS 100 | QS 100 | QS 100 |
| Polyquaternium-4[1] | 2.00 | 2.00 | 2.00 |
| Copolymer Premix of Example V[2] | 10.00 | 8.00 | 12.00 |
| Lauramide DEA | 0.33 | 0.33 | 0.33 |
| Sodium Methyl Oleyl Taurate | 1.67 | 1.67 | 1.67 |
| DMDM Hydantoin | 0.78 | 0.78 | 0.78 |
| Disodium EDTA | 0.20 | 0.20 | 0.20 |
| Polyoxyalkylated isostearyl Alcohol[3] | 0.10 | 0.10 | 0.10 |
| Fragrance | 0.10 | 0.10 | 0.10 |
| Propellant[4] | 7.0 | 7.0 | 7.0 |

[1]Available as Celquat H-100.
[2]Alternatively, mousse compositions are prepared using the Copolymer Premix of Example IV or VI.
[3]Available as Aerosurf 66-E10.
[4]Available as a mixture of 82.46% isobutane, 16.57% propane, and 0.001% butane.

These products are prepared by first dissolving the Polyquaternium-4 in water with stirring. The remaining ingredients, except the propellant, are then added with stirring.

The resulting mousse concentrate can then be combined with conventional propellants (e.g., Propellant A46) and packaged in an aerosol spray.

These mousses are useful for application to the hair to provide a styling and holding benefit.

EXAMPLE VIII

Hair Tonic

Hair tonic compositions are prepared from the following components utilizing conventional mixing techniques.

| Ingredients | Weight % | | |
|---|---|---|---|
| | A | B | C |
| Water | QS 100 | QS 100 | QS 100 |
| Cetyl Hydroxyethylcellulose[1] | 0.25 | 0.33 | 0.42 |
| Copolymer Premix of Example VI[2] | 3.00 | 4.00 | 5.00 |
| Fragrance | 0.10 | 0.20 | 0.30 |

[1]Available as Polysurf D-67
[2]Alternatively, tonic compositions are prepared using the Copolymer Premixes of Examples IV and V.

These products are prepared by dissolving the cetl hydroxyethylcellulose in the ethanol with stirring and then adding the fragrance and any colors.

These hair tonics are useful for application to the hair to provide a styling and holding benefit.

EXAMPLE IX

Hair Conditioner

A hair conditioner composition is prepared from the following components utilizing conventional mixing techniques.

| Ingredient | Weight % | |
|---|---|---|
| | A | B |
| Styling Agent Premix | | |
| Copolymer Premix of Example IV[1] | 10.00 | 10.00 |
| Silicone Premix | | |
| Silicone gum, GE SE76[2] | 0.30 | 0.30 |
| Octamethyl cyclotetrasiloxane | 1.70 | 1.70 |
| Main Mix | | |
| Water | QS100 | QS100 |
| Cetyl Alcohol | 1.00 | — |
| Quaternium 18[3] | 0.85 | 0.85 |
| Stearyl Alcohol | 0.70 | — |
| Hydroxethyl Cellulose | 0.50 | — |
| Cetyl Hydroxyethyl Cellulose[4] | — | 1.25 |
| Ceteareth-20 | 0.35 | — |
| Fragrance | 0.20 | 0.20 |
| Dimethicone copolyol | 0.20 | — |
| Citric Acid | 0.13 | 0.13 |
| Methylchloroisothiazolinone (and) methylisothiazolinone | 0.04 | 0.04 |
| Sodium Chloride | 0.01 | 0.01 |
| Xanthan Gum | — | 0.20 |

[1]Alternatively, conditioner compositions are prepared with polymer premixes from Example V and VI.
[2]Commercially available from General Electric.
[3]Dimethyl Di(Hydrogenated Tallow) Ammonium Chloride
[4]Commercially avaialbe as Polysurf D-67 from Aqualon.

The product is prepared by comixing all the Main Mix ingredients, heating to about 60° C. with mixing. The mixture is cooled to about 45° C. with colloid milling (Example A) or mixing (Example B). At this temperature, the two premixes are added separately with moderate agitation and the resulting conditioner is allowed to cool to room temperature.

This product is useful as a rinse off hair conditioner.

EXAMPLE X

Shampoo Composition

A shampoo composition is prepared from the following components utilizing conventional mixing techniques.

| Ingredients | Weight % |
|---|---|
| Styling Agent | |
| Copolymer Premix from Example V Premix | 15.00 |
| Silicone gum | 0.50 |
| Dimethicone, 350 cs fluid | 0.50 |
| Main Mix | |
| Water | QS100 |
| Ammonium lauryl sulfate | 11.00 |
| Cocamide MEA | 2.00 |
| Ethylene glycol distearate | 1.00 |
| Xanthan Gum | 1.20 |
| Methylchloroisothiazolinone (and) methylisothiazolinone | 0.04 |
| Citric Acid to pH 4.5 as needed | |

The Main Mix is prepared by first dissolving the xanthan gum in the water with conventional mixing. The remaining Main Mix ingredients are added and the Main Mix is heated to 150° F. with agitation for ½ hour. The Styling Agent and the Premix are then added sequentially with about 10 minutes of agitation between additions, and the entire mixture is stirred while the batch is cooled to room temperature. For varied particile size, the Styling Agent and Premix can be added at different times using either or both high shear mixing (high speed dispersator) or normal agitation.

This shampoos is useful for cleansing the hear and for providing a styling benefit.

EXAMPLE XI

Anti-Acne Composition

An anti-acne composition is made by combining the following components using conventional mixing technology.

| Ingredient | Weight % |
|---|---|
| Water | QS100 |
| Silated Hydroxyethylcellulose[1] | 1.0 |
| Salicylic Acid | 2.0 |
| Copolymer Premix from Example VI[2] | 4.0 |
| Ethanol (SDA 40) | 40.0 |

[1]Available from Aqualon.
[2]Alternatively, the anti-acne compositions are prepared using the Copolymer Premixs of Examples IV and V.

The compositon display skin penetration of the salicylic acid as well as improved skin reel and residue characteristics and is useful for the treatment of ache.

EXAMPLE XII

Topical Analgesic Composition

A topical analgesic composition is made by combining the following ingredients utilizing conventional mixing techniques.

| Ingredient | Weight % |
| --- | --- |
| Water, Purified | QS100 |
| Silated Hydroxyethylcellulose[1] | 0.5 |
| Ibuprofen | 2.0 |
| Copolymer Premix from Example VI[2] | 2.0 |
| Ethanol (SDA 40) | 20.0 |

[1] Available from Aqualon.
[2] Alternatively, the topical analagesic compositions are prepared using the Copolymer Premixs of Examples IV and V.

The compositions display skin penetration of the ibuprofen active as well as improved skin feel and residue characteristics together with excellent moisturizing, emolliency, rub-in and absorption characteristics.

EXAMPLE XIII

Sunless Tanning Composition

A composition for sunless tanning is made by combining the following ingredients utilizing conventional mixing techniques.

| Ingredients | Weight % |
| --- | --- |
| Phase A | |
| Water | qs 100 |
| Copolymer Premix from Example IV[1] | 5.00 |
| Carbomer 934[2] | 0.20 |
| Carbomer 980[3] | 0.15 |
| Acrylic Acid Copolymer[4] | 0.15 |
| Phase B | |
| PPG-20 Methyl Glucose Ether Distearate | 2.00 |
| Tocopheryl Acetate | 1.20 |
| Mineral Oil | 2.00 |
| Stearyl Alcohol | 1.00 |
| Shea Butter | 1.00 |
| Cetyl Alcohol | 1.00 |
| Ceteareth-20 | 2.50 |
| Ceteth-2 | 1.00 |
| Ceteth-10 | 1.00 |
| DEA-Cetyl Phosphate | 1.00 |
| Phase D | |
| Dihydroxyacetone | 3.00 |
| Phase E | |
| Butylene Glycol | 2.00 |
| DMDM Hydantoin (and) Iodopropynyl Butylcarbamate | 0.25 |
| Phase F | |
| Fragrance | 1.00 |
| Cyclomethicone | 2.00 |

[1] Alternatively, the artificial tanning compositions are prepared using the Copolymer Premixs of Examples V and VI.
[2] Available as Carbopol ® 934 from B. F. Goodrich.
[3] Available as Carbopol ® 980 from B. F. Goodrich.
[4] Available as Pemulen TR1 from B. F. Goodrich.

In a suitable vessel the Phase A ingredients are dispersed in the water and heated to 75°–85° C. In a separate vessel the Phase B ingredients are combined and heated to 85°–90° C. until melted. Next, the DEA-Cetyl Phosphate is added to the liquid Phase B and stirred until dissolved. This mixture is then added to Phase A to form the emulsion. The emulsion is cooled to 40°–45° C. with continued mixing. Next, in a separate vessel, the dihydroxyacetone is dissolved in water and the resulting solution is mixed into the emulsion. In another vessel, the Phase E ingredients are heated with mixing to 40°–45° C. until a clear solution is formed and this solution is then added to the emulsion. Finally, the Phase F ingredients are added to the emulsion with mixing, which is then cooled to 30°–35° C., and then to room temperature.

This emulsion is useful for topical application to the skin to provide an artificial tan.

EXAMPLE XIV

Sunscreen Composition

An oil-in-water emulsion is prepared by combining the following components utilizing conventional mixing techniques.

| Ingredients | Weight % |
| --- | --- |
| Phase A | |
| Water | QS100 |
| Carbomer 954[1] | 0.24 |
| Carbomer 1342[2] | 0.16 |
| Copolymer Premix from Example V[3] | 5.00 |
| Disodium EDTA | 0.05 |
| Phase B | |
| Isoarachidyl Neopentanoate[4] | 2.00 |
| PVP Eicosene Copolymer[5] | 2.00 |
| Octyl Methoxycinnamate | 7.50 |
| Octocrylene | 4.00 |
| Oxybenzone | 1.00 |
| Titanium Dioxide | 2.00 |
| Cetyl Palmitate | 0.75 |
| Stearoxytrimethylsilane (and) Stearyl Alcohol[6] | 0.50 |
| Glyceryl Tribehenate[7] | 0.75 |
| Dimethicone | 1.00 |
| Tocopheryl Acetate | 0.10 |
| DEA-Cetyl Phosphate | 0.20 |
| Phase C | |
| Water | 2.00 |
| Triethanolamine 99% | 0.60 |
| Phase D | |
| Water | 2.00 |
| Butylene Glycol | 2.00 |
| DMDM Hydantoin (and) Iodopropynyl Butylcarbamate[8] | 0.25 |
| dL Panthenol | 1.00 |
| Phase E | |
| Cyclomethicone | 1.00 |

[1] Available as Carbopol ® 954 from B. F. Goodrich.
[2] Available as Carbopol ® 1342 from B. F. Goodrich.
[3] Alternatively, the sunscreen compositions are prepared using the Copolymer Premixs of Examples IV and VI.
[4] Available as Elefac I-205 from Bernel Chemical.
[5] Available as Ganex V-220 from GAF Corporation.
[6] Available as DC 580 Wax from Dow Corning.
[7] Available as Synchrowax HRC from Croda.
[8] Available as Glydant Plus from Lonza.

In a suitable vessel the Phase A ingredients are dispersed in the water and heated to 75°–85° C. In a separate vessel the Phase B ingredients (except DEA-Cetyl Phosphate) are combined and heated to 85°–90° C. until melted. Next, the DEA-Cetyl Phosphate is added to the liquid Phase B and stirred until dissolved. This mixture is then added to Phase A to form the emulsion. The Phase C ingredients are combined until dissolved and then added to the emulsion. The emulsion is then cooled to 40°–45° C. with continued mixing. In another vessel, the Phase D ingredients are heated with mixing to 40°–45° C. until a clear solution is formed and this solution is then added to the emulsion. Finally, the emulsion is cooled to 35° C. and the Phase E ingredient is added and mixed.

This emulsion is useful for topical application to the skin to provide protection from the harmful effects of ultraviolet radiation.

EXAMPLE XV

Facial Moisturizer

A leave-on facial emulsion composition containing a cationic hydrophobic surfactant is prepared by combining the following components utilizing conventional mixing techniques.

| Ingredient | Weight % |
|---|---|
| Water | QS100 |
| Copolymer Premix from Example VI[1] | 1.00 |
| Glycerin | 3.00 |
| Cetyl Palmitate | 3.00 |
| Cetyl Alcohol | 1.26 |
| Quaternium-22 | 1.00 |
| Glyceryl Monohydroxy Stearate | 0.74 |
| Dimethicone | 0.60 |
| Stearic Acid | 0.55 |
| Octyldodecyl Myristate | 0.30 |
| Potassium Hydroxide | 0.20 |
| Carbomer 1342 | 0.125 |
| Tetrasodium EDTA | 0.10 |
| DMDM Hydantoin and Iodopropynyl Butyl Carbamate | 0.10 |
| Carbomer 951 | 0.075 |

[1]Alternatively, the moisturizers are prepared using the Copolymer Premixes of Examples IV and V.

This emulsion is useful for application to the skin as a moisturizer.

EXAMPLE XVI

Nail Polish Composition

A nail polish composition is made by combining the following ingredients utilizing conventional mixing techniques.

| Ingredient | Weight % |
|---|---|
| Copolymer Premix from Example VI | 30.0 |
| Ethanol (SDA 40) | 10.0 |
| Dibutyl Phthalate | 5.0 |
| n-Butyl Acetate | 25.0 |
| Ethyl Acetate | 8.0 |
| D&C Yellow #10 Aluminum Lake | 0.5 |
| Toluene | q.s. |

What is claimed is:

1. A topical personal care composition, said composition comprising:

(a) a polysiloxane-grafted adhesive polymer;

(b) a volatile, water insoluble solvent for said polysiloxane-grafted polymer;

(c) a nonvolatile drying aid for said polysiloxane grafted polymer which is soluble in said solvent (b) at 45° C. and is water insoluble at 25° C., and is selected from the group consisting of silicone fluids and waxes having from 1 to about 100 siloxy units, silanes, and silicone resins, and mixtures thereof;

wherein the weight ratio of said polysiloxane-grafted adhesive polymer to said drying aid is about 100:1 or less.

2. A composition as in claim 1, wherein the weight ratio of polysiloxane-grafted adhesive polymer to said drying aid is from about 5:1 to about 75:1.

3. A composition as in claim 2, wherein the weight ratio of said polysiloxane-grafted adhesive polymer to said drying aid is from about 7:1 to about 50:1.

4. A composition as in claim 3, wherein the weight ratio of said polysiloxane-grafted adhesive polymer to said drying aid is from about 10:1 to about 35:1.

5. A composition as in claim 2, wherein said volatile solvent (b) is a silicone fluid.

6. A composition as in claim 5, wherein said volatile solvent is cyclopolydimethylsiloxane.

7. A composition as in claim 1, wherein said drying aid is silicone resin.

8. A composition as in claim 4, wherein said drying aid is a silicone resin.

9. A composition as in claim 5, wherein said drying aid is a silicone resin.

10. A composition as in claim 9, wherein said silicone resin has a ratio of oxygen to silicon atoms, calculated on a molar basis, of at least about 1.2:1.0.

11. A composition as in claim 10, wherein said silicone resin is an MQ silicone resin having an average molecular weight from about 1000 to about 10,000.

12. A composition as in claim 5, wherein said volatile solvent (b) has a boiling point at one atmosphere of about 250° C. or less.

13. A composition as in claim 12, wherein said boiling point of said volatile solvent (b) is about 230° C. or less.

14. A topical personal care composition sutiable for application to the skin or hair, said composition comprising:

(a) a polysiloxane-grafted adhesive polymer;

(b) a volatile, water insoluble solvent for said polysiloxane-grafted polymer;

(c) a nonvolatile drying aid for said polysiloxane grafted polymer which is soluble in said solvent (b) at 45° C. and is water insoluble at 25° C., and is selected from the group consisting of silicone fluids and waxes having from 1 to about 100 siloxy units, silanes, and silicone resins, and mixtures thereof;

wherein said components (a), (b), and (c) form a dispersed phase of droplets in a carrier comprising water, a water soluble liquid, or a mixture thereof.

15. A composition as in claim 14, further comprising a thickening agent, or gelling agent.

16. A composition as in claim 14, further comprising a hair or skin conditioning agent selected from the group consisting of silicone fluids, cationic surfactants and polymers, and nonvolatile organic oils, and mixtures thereof.

17. A method for styling hair comprising applying an effective amount of the composition of claim 1 to the hair for styling said hair, arranging the style of the hair prior to, during, or after application of said composition, and drying said composition.

18. A method as in claim 18 wherein said composition is dried at a temperature of about 45° C. or higher.

19. A method for styling hair comprising applying an effective amount of the composition of claim 14 to the hair for styling said hair, arranging the style of the hair prior to, during, or after application of said composition, and drying said composition.

20. A method as in claim 19 wherein said composition is dried at a temperature of about 45° C. or higher.

21. A method for treating skin or nails comprising applying an effective amount of the composition of claim 1 to skin or nails to form a film of said polysiloxane grafted polymer on said skin or nails.

22. A method as in claim 21, wherein said composition is dried by heatin to 45° C. or higher.

23. A composition as in claim 1, wherein the drying aid is a silicone fluid having a viscosity of 100,000 cs or less at 25° C.

* * * * *

UNITED STATES PATENT AND TRADEMARK OFFICE
CERTIFICATE OF CORRECTION

PATENT NO. : 5,567,428

DATED : October 22, 1996

INVENTOR(S) : Kendrick Jon Hughes

Page 1 of 2

It is certified that error appears in the above-indentified patent and that said Letters Patent is hereby corrected as shown below:

Column 1, line 30 "siloxane-grafied" should read --siloxane-grafted--.

Column 1, line 44 "Apr. 14, 1992, and" should read --Apr. 14, 1992.--.

Column 4, line 55 "following four criteria" should read --following criteria--.

Column 5, line 18 "therein." should read --therein).--

Column 6, line 8 " and the all of which" should read -- all of which--.

Column 8, line 57 "mixture,, thereof" should read --mixtures thereof--.

Column 9, line 51 "pp. 27-32" should read --pp. 27-32.--.

Column 10, line 1 "decerie" should read --decene--.

Column 10, line 7 "hydrocarbons, Examples" should read --hydrocarbons. Examples--.

Column 10, line 10 "Isopar™ and K" should read --Isopar™ H and K--.

Column 11, lines 40-41 "426, both incorporated herein by reference." should read --426.--.

Column 13, line 32 "dimethic, one, and" should read --dimethicone, and--.

Column 13, line 37 "and shod chain" should read --and short chain--.

Column 18, line 28 "surfactant⇔ is" should read --surfactant" is--.

Column 18, line 65 "$CH_3\text{-}(CH2)\text{-}CH2\text{-}(OCH2CH2)_n\text{-}OH$" should read --$CH_3\text{-}(CH2)14\text{-}CH2\text{-}(OCH2CH2)_n\text{-}OH$--.

Column 19, line 63 "acids estertried with" should read --acids esterified with--.

Column 21, line 14 "one shod" should read --one short--.

Column 21, line 32 "documents, all incorporated by reference herein:" should read --documents:--.

Column 23, line 28 "Nalkyltaurines" should read --N-alkyltaurines--.

UNITED STATES PATENT AND TRADEMARK OFFICE
CERTIFICATE OF CORRECTION

PATENT NO. : 5,567,428
DATED : October 22, 1996
INVENTOR(S) : Kendrick Jon Hughes It is certified that error appears in the above-indentified patent and that said Letters Patent is hereby corrected as shown below:

Column 25, line 45 "Br, I, or F" should read --Br, I, or F--.

Column 25, line 46 "Br, or I)" should read --Br, or I)--.

Column 26, line 15 "a shod chain" should read --a short chain--.

Column 27, line 11 "$R^1, R^2, R^3$ is an" should read --R is an--.

Column 29, line 15 "acids, A variety" should read --acids. A variety--.

Column 29, line 29 "peadescent" should read --pearlescent--.

Column 30, line 23 "50°C. or 0 higher" should read --50°C or higher--.

Column 34, line 67 "treatment of ache" should read --treatment of acne--.

Signed and Sealed this

Seventh Day of January, 1997

Attest:

BRUCE LEHMAN

*Attesting Officer*  *Commissioner of Patents and Trademarks*